US012810512B2

(12) United States Patent
Cierniak

(10) Patent No.: US 12,810,512 B2
(45) Date of Patent: Nov. 24, 2026

(54) STATISTICAL RECONSTRUCTION METHOD BASED ON A CONTINUOUS-TO-CONTINUOUS DATA MODEL WITH ITERATIVE COORDINATE DESCENT OPTIMIZATION STRATEGY FOR EMISSION TOMOGRAPHY

(71) Applicant: CZESTOCHOWA UNIVERSITY OF TECHNOLOGY, Częstochowa (PL)

(72) Inventor: Robert Cierniak, Częstochowa (PL)

(73) Assignee: CZESTOCHOWA UNIVERSITY OF TECHNOLOGY, Czestochowa (PL)

( * ) Notice: Subject to any disclaimer, the term of this patent is extended or adjusted under 35 U.S.C. 154(b) by 204 days.

(21) Appl. No.: 18/412,591

(22) Filed: Jan. 14, 2024

(65) Prior Publication Data

US 2025/0232491 A1 Jul. 17, 2025

(51) Int. Cl.
*G06T 12/30* (2026.01)
*A61B 6/03* (2006.01)
*G06T 12/20* (2026.01)

(52) U.S. Cl.
CPC .............. *G06T 12/20* (2026.01); *A61B 6/037* (2013.01); *G06T 12/30* (2026.01); *G06T 2210/41* (2013.01); *G06T 2211/424* (2013.01)

(58) Field of Classification Search
CPC ..... A61B 6/037; G06T 11/006; G06T 11/008; G06T 2210/41; G06T 2211/424
See application file for complete search history.

(56) References Cited

U.S. PATENT DOCUMENTS 6,055,291 A * 4/2000 Hu .......................... G06T 12/10 378/19
9,508,164 B2 * 11/2016 Cierniak ................ G06T 12/20
10,573,029 B2 * 2/2020 Cierniak ................ G06T 12/20
2009/0123048 A1 * 5/2009 Leroux .................. G06T 12/20 250/363.04
2012/0051626 A1 * 3/2012 Long ...................... G06T 12/20 382/154

(Continued)

OTHER PUBLICATIONS

K. Sauer, C. Bouman: A local update strategy for iterative reconstruction from projections, IEEE Transactions on Signal Processing, vol. 41, No. 3, pp. 534-548, 1993.

(Continued)

*Primary Examiner* — Tsung Yin Tsai
(74) *Attorney, Agent, or Firm* — Andrzej Malarz, Esq.

(57) ABSTRACT

An iterative statistical algorithm based on a continuous-to-continuous data model with iterative coordinate descent optimization for image reconstruction from radiation measurements obtained in emission tomography, i.e. in a Positron Emission Tomography scanner, is described in this invention. The method presented here improves the resolution of the reconstructed images and/or decreases the tracer dosage absorbed by a patient during examination. At the same time, it maintains the quality of the functional images obtained. Additionally, this method allows for the presence of the regularization as an additive term. Furthermore, this method makes it possible to control the convergence of the algorithm using a specific parameter. These improvements are due to the signals obtained regarding the given statistics of this imaging technique.

2 Claims, 7 Drawing Sheets

(56) References Cited

U.S. PATENT DOCUMENTS

| | | | | |
|---|---|---|---|---|
| 2013/0343673 | A1* | 12/2013 | Pal | G06T 12/00<br>382/298 |
| 2018/0082446 | A1* | 3/2018 | Chinomi | G06T 12/20 |
| 2019/0206094 | A1* | 7/2019 | Cierniak | G06T 12/20 |

OTHER PUBLICATIONS

J. A. Fessler: Penalized weighted least-squares image reconstruction for positron emission tomography, IEEE Transactions on Medical Imaging, vol. 13, No. 2, pp. 290-300, 1994.

L. A. Shepp, Y. Vardi: Maximum likelihood reconstruction for emission tomography, IEEE Transactions on Medical Imaging, vol. MI-1, No. 2, pp. 113-122, 1982.

P. J. Green: Bayesian reconstructions from emission tomography data using a modified EM algorithm, IEEE Transactions on Medical Imaging, vol. 9, No. 1, pp. 84-93, 1990.

R. Cierniak: New neural network algorithm for image reconstruction from fan-beam projections, Neurocomputing, vol. 72, pp. 3238-3244, 2009.

R. Cierniak: A new approach to tomographic image reconstruction using a Hopfield-type neural network, International Journal Artificial Intelligence in Medicine, vol. 43, No. 2, pp. 113-125, 2008.

R. Cierniak: A three-dimensional neural network based approach to the image reconstruction from projections problem, Lecture Notes in Artificial Intelligence 6113, s. 505-514, Springer Verlag, 2010.

Dobosz P., Cierniak R: Using of EM algorithm to image reconstruction problem with tomography noises, 5th International Conference on Image Processing & Communications, Bydgoszcz, 11-13. IX.2013, In: Image Processing and Communications Challenges 5. Ed. Ryszard S. Choras, pp. 37-43, Advances in Soft Computing Series, vol. 233, Springer, Cham, 2013.

Zeng L.: Extension of emission EM look-alike algorithms to Bayesian Algorithms, 17th International Meeting on Fully Three-Dimensional Image Reconstruction in Radiology and Nuclear Medicine, Proc. SPIE vol. 11072, 2019.

* cited by examiner

STATISTICAL RECONSTRUCTION METHOD BASED ON A CONTINUOUS-TO-CONTINUOUS DATA MODEL WITH ITERATIVE COORDINATE DESCENT OPTIMIZATION STRATEGY FOR EMISSION TOMOGRAPHY

TECHNICAL FIELD

Invention relates to medical positron emission tomography, and particularly to the reduction of the radiotracer dosage in imaging techniques belonging to this category.

BACKGROUND OF THE INVENTION

Medical imaging is one of the most useful diagnostic tools available to medicine. The invention presented here relates to one of the most popular imaging techniques belonging to the emission tomography category: positron emission tomography (PET). This medical imaging technique allows us to look inside a person and obtain images that illustrate various biological processes and functions. In this technique, a patient is initially injected with a radiotracer, which contains bio-chemical molecules. These molecules are tagged with a positron emitting radioisotope, and can participate in physiological processes in the body. After the decay of these radioisotope molecules, positrons are emitted from the various tissues of the body which have absorbed the molecules. As a consequence of the annihilation of the positrons, pairs of gamma photons are produced and are released in opposite directions. In PET scanners, these pairs of photons are registered by detectors and counted. A pair of detectors detecting a pair of gamma photons at the same time constitutes a line of response (LOR). A count of photons registered on a certain LOR will be called a projection. Data associated with annihilation events along different LORs are collected and processed. A given set of projections is mostly formed as a so-called sinogram based on their corresponding LORs.

The goal of the PET is to reconstruct the distribution of the radiotracer in the tissues of the investigated cross-sections of the body based on a set of projections from various LORs obtained by the PET scanner. The problem formulated in this way is called an image reconstruction from projections problem and is solved using various reconstruction methods. Because of the relatively small number of annihilations observed in a single LOR, the statistical nature of the measurements performed has a strong influence and must be taken into account. Recently, some new concepts regarding reconstruction algorithms have been applied to emission tomography techniques (i.e. to positron emission tomography (PET)), with statistical approaches to image reconstruction being particularly preferred (see e.g. [1], [2]). The standard reconstruction method used in PET is the maximum likelihood—expectation maximization (ML-EM) algorithm, as described for example in [3][4]. In this algorithm an iterative procedure is used in the reconstruction process, as follows:

$$f_l^{t+1} = f_l^t \frac{1}{\sum_k a_{kl}} \sum_k a_{kl} \frac{\lambda_k}{\sum_{l'} a_{kl'} f_{l'}^t}, \tag{1}$$

where: $f_l$ is an estimate of the image representing the distribution of the radiotracer in the body; l=1, . . . , L is an index of pixels; t is an iteration index; $\lambda_k$ is the number of annihilation events detected along the k-th LOR; $a_{kl}$ is an element of the system matrix.

It should be underlined that using this algorithm it is impossible to control the speed of its convergence, and in consequence, to use so called "early stopping" regularization strategy.

Modification of this method, i.e. using ordered subset expectation maximization (OSEM), and improvements in computing speed, have allowed for iterative algorithms to be used in the standard clinical practice of PET devices.

Because reconstruction problem (1) is ill-conditioned, it is possible to use a regularization of it, according to the following relation (see e.g. [9]):

$$f_l^{t+1} = f_l^t \frac{1}{\sum_k a_{kl} + \beta R_l^t} \sum_k a_{kl} \frac{\lambda_k}{\sum_{l'} a_{kl'} f_{l'}^t}, \tag{2}$$

where:

$$R_l^t$$

is the derivative of a penalty function V with respect to the image pixel $$f_l^t;$$

β is a control parameter.

It should be underlined that the above form of regularization is very inconvenient for a computer implementation of the algorithm (2).

This algorithm is presented in the literature as being more robust and flexible than analytical inversion methods because it allows for accurate modeling of the statistics of the measurements obtained in the PET, i.e. the Poisson statistical distribution of the annihilations detected on the LORs.

The image processing methodology used in this algorithm is consistent with the discrete-to-discrete data model, where the reconstructed image is conceptually divided into homogeneous blocks representing pixels. In this conception, the elements of the system matrix $a_{kl}$ are determined for every pixel l separately, for every annihilation event $\lambda_k$ detected along the k-th LOR. Bearing in mind the non-zero width of the radiation detector, it is easy to ascertain the set of image blocks that have an influence on the formation of the measurement $\lambda_k$. The next step is to consider the contribution made by each image block to the way in which each LOR passes through. This contribution can be calculated, for example, by counting the sub-blocks of a given block l through which the LOR k passes. Unfortunately, this reconstruction problems are formulated using matrices with very large dimensionality. This reconstruction algorithm is thus much more complex than analytical methods.

The author of this invention has devised a new statistical approach to the image reconstruction problem, which is consistent with a continuous-to-continuous data model. The problem as formulated by the author of this invention can be defined as an approximate discrete 2D reconstruction problem (see e.g. [5]). It takes into consideration a form of the interpolation function used in back-projection operations.

The preliminary conception of this kind of image reconstruction from projections strategy for transmission tomography, i.e. x-ray computed tomography (CT), is represented in the literature only in the original works published by the author of this invention, for parallel scanner geometry (see e.g. [6]), for fan-beam geometry (see e.g. [5]) and for spiral cone-beam tomography (see e.g. [7]). The reconstruction procedure used for a spiral cone-beam CT scanner has been patented in 2016 (see U.S. Pat. No. 9,508,164 B2). In consequence of the analytical origins of the reconstruction method proposed in the above papers, most of the above-mentioned difficulties connected with using algebraic methodology can be avoided. Although the proposed reconstruction method has to establish certain coefficients, these can be pre-calculated and, because of the small memory requirements, can be stored in memory. Generally, because of the use of the discrete-to-discrete data model, the coefficients $a_{kl}$ are calculated dynamically during the reconstruction process, because of the huge dimensionality of the matrix containing these elements of the system. The analytical (with the continuous-to-continuous data model) reconstruction problem is formulated as a shift-invariant system, which allows the application of a FFT algorithm during the most demanding calculations, and in consequence, significantly accelerates the image reconstruction process.

In the case of emission tomography, e.g. the PET, the measurements obtained from the scanner are subject directly to statistics consistent with the Poisson distribution. This means that the preferred approaches for this imaging technique (using the ML method) are based on the Kullback-Leibrer divergence, and the EM algorithm associated with it. This invention is strictly concerned with the analytical reconstruction approach previously devised for the transmission CT technique, and the adoption of this solution to the emission PET imaging technique, using an EM algorithm with an analytical scheme of image processing. Previously, an attempt has been made to develop the idea of an iterative statistical approach with an analytical image processing framework for the CT technique in the direction of the EM method [8]. That algorithm has been previously patented in 2020 (see U.S. Pat. No. 10,573,029 B2) in the following form:

$$f_{i,j}^{t+1} = f_i^t \frac{1}{g_{ij}} \sum_i \sum_j \frac{\tilde{f}_{i,j}}{\sum_{i'} \sum_{j'} f_{ij}^t h_{\Delta i,\Delta j}} h_{\Delta i,\Delta j}, \quad (3)$$

where: $f_{i,j}$ is an estimate of the image representing the distribution of the radiotracer in the body; i=1, 2, . . . , I; j=1, 2, . . . , I; I is a dimension of the image; $\tilde{f}_{i,j}$ is the image of the cross-section obtained after the back-projection operation at position; $h_{\Delta i,\Delta j}$ is the coefficients matrix, Δi (Δj) is the difference between the index of pixels in the x direction (y direction); $g_{ij}$ is a scaling matrix which is determined based on the matrix of the coefficients $h_{\Delta i,\Delta j}$.

However, it is impossible to use the formula (3) to control the speed of convergence of it, and in consequence, to use so called "early stopping" regularization strategy (without any regularization term). Although, it is possible to use a regularization of the formula (3) according to the following relation:

$$f_{i,j}^{t+1} = f_{i,j}^t \frac{1}{g_{ij} + \beta R_{ij}^t} \sum_i \sum_j \frac{\tilde{f}_{ij}}{\sum_{i'} \sum_{j'} f_{ij}^t h_{\Delta i,\Delta j}} h_{\Delta i,\Delta j}, \quad (4)$$

but the above form of regularization is very inconvenient for a computer implementation of this iterative algorithm.

There is proposed a new form of the statistical reconstruction method based on a continuous-to-continuous data model with iterative coordinate descent strategy to overcome the above problems in this patent, as follows:

$$f_{i,j}^{t+1} = f_{i,j}^t - \rho \left( \sum_i \sum_j \frac{\tilde{f}_{ij}}{\sum_{i'} \sum_{j'} f_{ij}^t h_{\Delta i,\Delta j}} h_{\Delta i,\Delta j} - g_{ij} \right), \quad (5)$$

where ρ is a coefficient.

It is possible using formula (5) to control the speed of its convergence to a solution, and, in consequence, it allows for using so-called "early stopping" regularization strategy. Additionally, it is possible to use an additive regularization term according to the Tikhonov approach, as follows:

$$f_{i,j}^{t+1} = f_{i,j}^t - \rho \left( \sum_i \sum_j \frac{\tilde{f}_{ij}}{\sum_{i'} \sum_{j'} f_{ij}^t h_{\Delta i,\Delta j}} h_{\Delta i,\Delta j} - g_{ij} \right) - \beta R_{i,j}^t, \quad (6)$$

This form of the algorithm is relatively easy for a computer implementation.

BRIEF DESCRIPTION OF THE INVENTION

Figure 1:
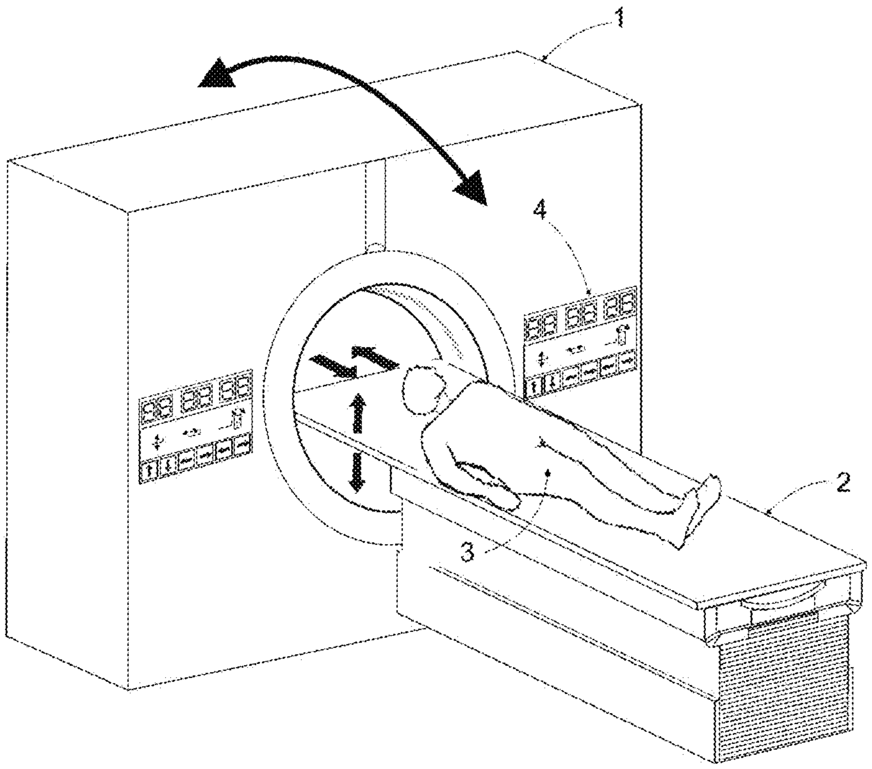
FIG. 1 shows a general view of a PET scanner.

In contrast to the iterative statistical ML-EM reconstruction procedure, based on a discrete-to-discrete data model, as described by Eq. (1), the reconstruction method proposed in this invention is based on a continuous-to-continuous data model, as follows:

$$f_{i,j}^{t+1} = f_{i,j}^t - \rho \left( \sum_i \sum_j \frac{\tilde{f}_{ij}}{\sum_{i'} \sum_{j'} f_{ij}^t h_{\Delta i,\Delta j}} h_{\Delta i,\Delta j} - g_{ij} \right), \quad (7)$$

$f_{i,j}$ is an estimate of the image representing the distribution of the radiotracer in the body; i=1, 2, . . . , I; j=1, 2, . . . , I; I is a dimension of the image; $\tilde{f}_{i,j}$ is the image of the cross-section obtained after the back-projection operation at position; $h_{\Delta i,\Delta j}$ is the coefficients matrix, Δi (Δj) is the difference between the index of pixels in the x direction (y direction); $g_{ij}$ is a scaling matrix which is determined based on the matrix of the coefficients $h_{\Delta i,\Delta j}$, ρ is a coefficient.

The analytical character of this method is due to the form of the reconstruction problem, i.e. as a shift invariant problem (see e.g. [5]). It uses a form of interpolation function used in the back-projection operation. All the geometrical conditions of the measurements are fitted into a matrix of coefficients, which is determined numerically, based on the above-mentioned interpolation function. Because of this, the proposed method has several advantages over the ML-EM reconstruction procedure. Firstly, it is possible to move the most demanding parts of the calculations into the frequency domain. This is done using 2D FFT and 2D IFFT algorithms during every iteration performed by the iterative reconstruction procedure. Moreover, although the proposed reconstruction method must establish the coefficients, that can be performed much more easily than in comparable methods. It is possible using formula (5) to control the speed of its convergence to a solution, and, in consequence, it allows for using so-called "early stopping" regularization strategy. Additionally, it is possible to use an additive regularization term according to the Tikhonov approach, as follows:

$$f_{i,j}^{t+1} = f_{i,j}^{t} - \rho\left(\sum_i \sum_j \frac{\tilde{f}_{ij}}{\sum_{i'} \sum_{j'} f_{ij}^{t} h_{\Delta i,\Delta j}} h_{\Delta i,\Delta j} - g_{ij}\right) - \beta R_{i,j}^{t}, \tag{8}$$

where:

$$R_l^t$$

is the derivative of a penalty function V with respect to the image pixel $$f_l^t;$$

β is a control parameter.

The method for reconstructing the image of an examined object using measurements obtained by a PET scanner comprises: establishing a gamma radiation detector array, calculating the coefficients of the matrix $h_{\Delta i,\Delta j}$ and transforming this matrix into the matrix $H_{k,l}$ in the Fourier domain, determining the scaling matrix $g_{i,j}$ based on the matrix of the coefficients $h_{\Delta i,\Delta j}$, measuring the gamma radiation from a patient's body by using a PET scanner to obtain a projection dataset, performing a rebinning operation to transform the measurements obtained by the scanner with whatever geometry into the parallel geometry of the virtual measurements, performing a back-projection operation for a fixed cross-section of the examined object, and performing an iterative reconstruction procedure.

During the iterative reconstruction procedure, in every iteration, a 2D FFT is performed on the processed image to transform it into the frequency domain. Next, the elements of the frequency representation of the reconstructed image are multiplied by the corresponding elements of the matrix $H_{k,l}$. After this, a 2D IFFT of the resulting matrix of these multiplications is performed, establishing a referential image. Every element of the matrix representing the image obtained after the back-projection operation is divided by the corresponding elements of the referential image. Next, a 2D FFT is performed on the matrix resulting from this division. The elements of the frequency representation of the resulting matrix of the above-mentioned division are then multiplied by the corresponding elements of the matrix $H_{k,l}$. A 2D IFFT of the resulting matrix of these multiplications is performed, establishing a biased correction matrix. After this, from every element of the biased correction matrix the corresponding element of the matrix $g_{i,j}$ is subtracted, establishing a correction matrix. Next, every element of the matrix representing the reconstructed image is corrected by subtracting the corresponding element of the correction matrix multiplied by a constant coefficient from the value of this element. A criterion for stopping the iterative process is implemented. No geometric correction of the measurements obtained from the PET scanner is performed.

The coefficients $h_{\Delta i,\Delta j}$ used in the iterative reconstruction process are established according to the following relation:

$$h_{\Delta i,\Delta j} = (\Delta_{xy})^2 \Delta_{\alpha'} \sum_{\theta} \mathrm{Int}(|\Delta i| \cdot \Delta_{xy} \cos(\theta \cdot \Delta_{\alpha'}) + |\Delta j| \cdot \Delta_{xy} \sin(\theta \cdot \Delta_{\alpha'})), \tag{9}$$

where: Δi (Δj) is the difference between the index of pixels in the x direction (y direction); $\Delta_{xy}$ is the distance between pixels in the reconstructed image; $\Delta_{\alpha'}$ is an angular raster;

$$\theta = 0, 1, \ldots, \frac{2\pi}{\Delta_{\alpha'}} - 1$$

is the index of the angles; Int is an interpolation function used in the back-projection operation.

A plane is oriented, an image is placed in a coordinate system (x,y), and the topology of the pixels in the reconstructed image is placed according to the following description (see FIG. 6):

$$x = \ldots, -\frac{5\Delta_{xy}}{2}, -\frac{3\Delta_{xy}}{2}, -\frac{\Delta_{xy}}{2}, \frac{\Delta_{xy}}{2}, \frac{3\Delta_{xy}}{2}, \frac{5\Delta_{xy}}{2}, \ldots,$$

for the x direction, and $$y = \ldots, -\frac{5\Delta_{xy}}{2}, -\frac{3\Delta_{xy}}{2}, -\frac{\Delta_{xy}}{2}, \frac{\Delta_{xy}}{2}, \frac{3\Delta_{xy}}{2}, \frac{5\Delta_{xy}}{2}, \ldots$$

for the y direction, where $\Delta_{xy}$ is the distance between pixels in the reconstructed image, for both x and y directions. The reconstructed image has dimensions I×I (I is chosen to be equal to a positive integer power of 2).

DETAILED DESCRIPTION

Figure 2:
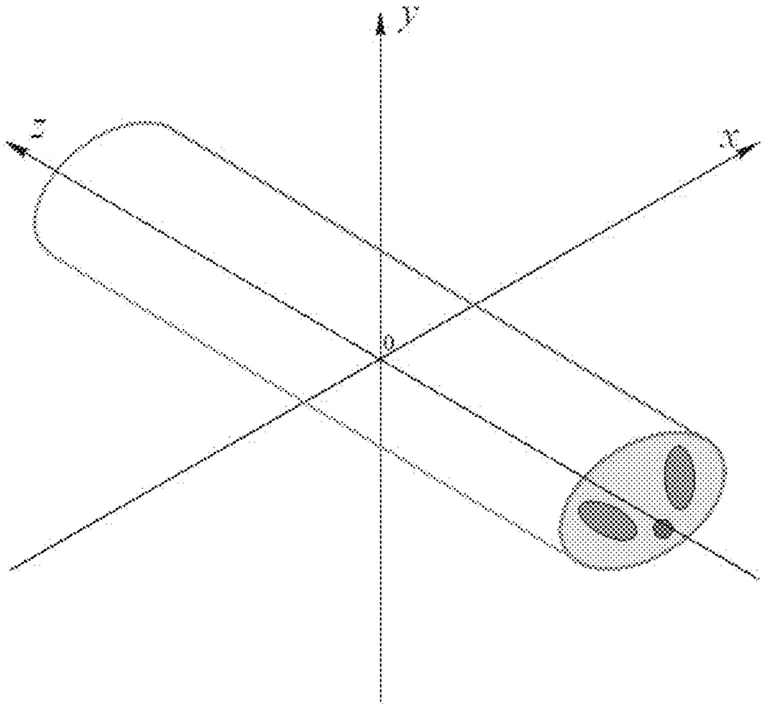
FIG. 2 depicts the orientation in the x-y-z coordinates of the measurement system of a PET scanner, in a three-dimensional perspective view.
Figure 3:
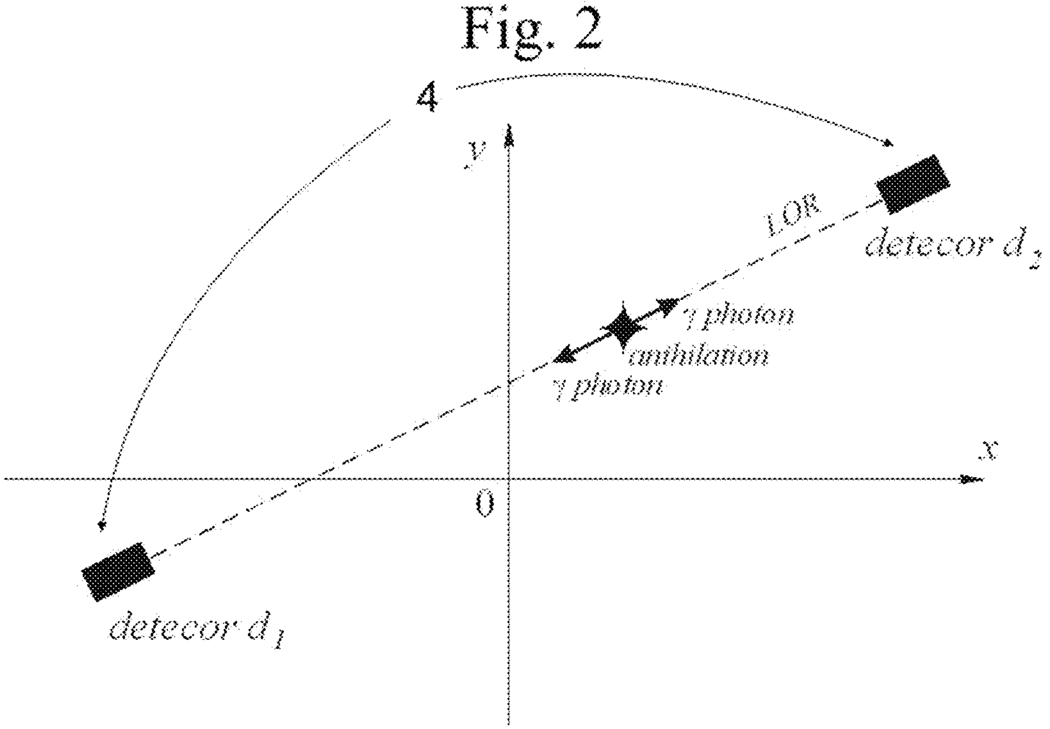
FIG. 3. shows the geometry of a line of response.
Figure 4:
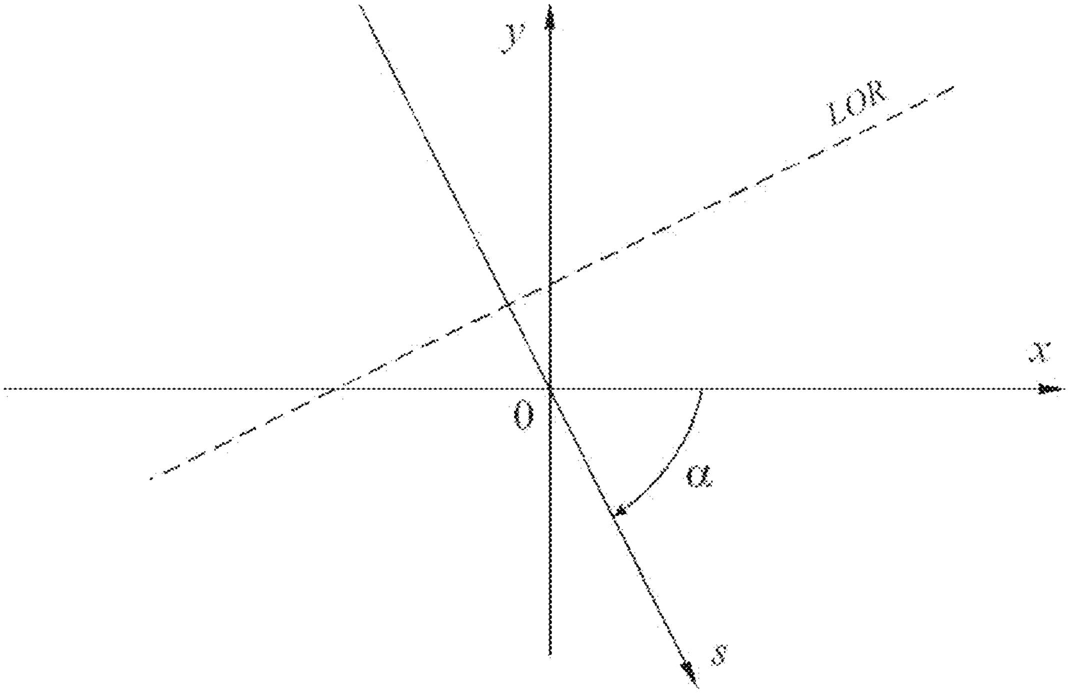
FIG. 4. depicts the parameters of a line of response related to the reconstruction plane.

A general scheme of the PET apparatus is shown in FIG. 1. The apparatus consists of three main parts: a positron emission tomography (PET) scanner 1, a support or couch 2 (on which the patient to be examined is placed), and a computer 3 (which is used to control the whole device and perform the reconstruction procedure). The image reconstruction method described here is carried out using the count of the gamma photon pairs, which is obtained by the measuring system installed in the scanner 1. FIG. 2 shows the projection system of the PET scanner in a three-dimensional perspective view oriented in an x-y-z coordinate system. The pair of detectors simultaneously detecting the pair of gamma photons constitutes a line of response (LOR) and is depicted in FIG. 3. Every measurement registers photons on a particular LOR using pairs of detectors 4. placed around the patient. Data associated with annihilation events along different LORs are collected and then processed. These direct measurements are processed statistically and then the input signals for the reconstruction procedure are obtained, denoted below as λ(s, α), where s and a are parameters of a given LOR in the rotated coordinate system x-y, as is depicted in FIG. 4. Next, all the signals λ(s, α) obtained are used for the reconstruction of the cross-section with its center located at the position $z_p$, as is indicated in FIG. 2, using the algorithm described by FIG. 5.

Having all the values λ(s, α), the reconstruction algorithm 4 can be started, as specified in the following steps.

Step 1

Figure 5:
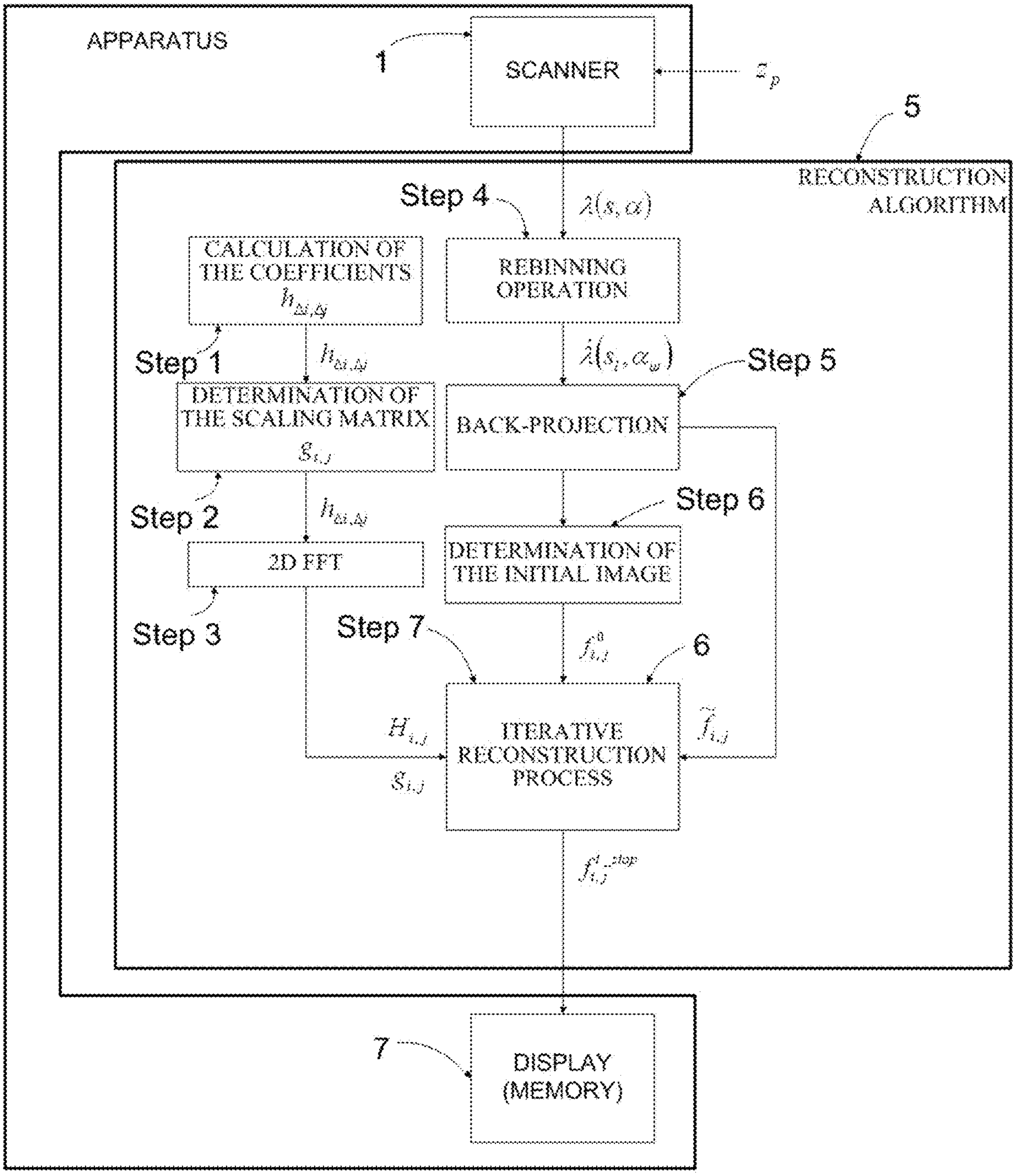
FIG. 5. depicts the block schematic diagram of a method used to practice the present invention, showing a connection to a computed tomography apparatus.

Before the main reconstruction procedure is started, the $h_{\Delta i,\Delta j}$ coefficients matrix is established (see FIG. 5). All of the calculations in this step of the reconstruction procedure can be pre-calculated, i.e. they can be carried out before the scanner performs any measurements. We make the simplification that the coefficients $h_{\Delta i,\Delta j}$ are the same for all pixels of the reconstructed image, and they can be calculated numerically, as follows:

$$h_{\Delta i,\Delta j} = (\Delta_{xy})^2 \Delta_{\alpha'} \sum_{\theta} \mathrm{Int}(|\Delta i| \cdot \Delta_{xy} \cos(\theta \cdot \Delta_{\alpha'}) + |\Delta j| \cdot \Delta_{xy} \sin(\theta \cdot \Delta_{\alpha'})), \quad (10)$$

where: Δi (Δj) is the difference between the index of pixels in the x direction (y direction); $\Delta_{xy}$ is the distance between the pixels in the reconstructed image; $\Delta_\alpha$ is the raster of angles of rotation;

$$\theta = 0, 1, \ldots, \frac{2\pi}{\Delta_{\alpha'}} - 1;$$

Int is an interpolation function.

In general, the interpolation function Int can be any interpolation function. In this invention, it is the ordinary linear interpolation function, which is expressed in the following way:

$$\mathrm{Int}(\Delta) = \begin{cases} \frac{1}{\Delta_{xy}}\left(1 - \frac{|\Delta|}{\Delta_{xy}}\right) & \text{for } |\Delta| \le \Delta_{xy} \\ 0 & \text{for } |\Delta| > \Delta_{xy} \end{cases}. \quad (11)$$

All the calculations in this step of the reconstruction procedure presented here can be pre-calculated, i.e. they can be carried out before the scanner performs any of the necessary measurements.

The output for this step is a matrix with the coefficients $h_{\Delta i,\Delta j}$. If the reconstructed image has dimensions I×I then this matrix has dimensions 2I×2I.

Step 2

In this step, a scaling matrix $g_{i,j}$ is determined based on the matrix of the coefficients $h_{\Delta i,\Delta j}$, obtained in Step 1. If the reconstructed image has dimensions I×I then this operation is performed according to the relation:

$$g_{i,j} = \sum_{\Delta i=i+1}^{I-i} \sum_{\Delta j=j+1}^{I-j} h_{\Delta i,\Delta j}. \quad (12)$$

All the calculations in this step of the presented reconstruction procedure can be pre-calculated, i.e. they can be carried out before the scanner performs any of the necessary measurements.

The output of this step is the scaling matrix $g_{i,j}$; i=1, 2, . . . , I; j=1, 2, . . . , I.

Step 3

In this step the matrix of the coefficients $h_{\Delta i,\Delta j}$ is transformed into the frequency domain using a 2D FFT transform (see FIG. 5). All the calculations in this step of the presented reconstruction procedure can be pre-calculated, i.e. they can be carried out before the scanner performs any of the necessary measurements.

The output of this step is a matrix of the coefficients $H_{k,l}$ with dimensions 2I×2I.

Step 4

The reconstruction procedure presented below relates to the so-called rebinning methodology, where the image is reconstructed from a set of virtual parallel projections and the calculation is based on real measurements. In this rebinning operation, we will first of all consider the parallel-beam raster determined by the pair $(s_l, \alpha_\psi)$, where: $s_l=(l-0.5)\cdot\Delta_{xy}$; l=−L/2, . . . , L/2 is the sample index of the detectors in a hypothetical parallel-beam system; L is an even number of virtual detectors, and $\alpha_\psi=\psi-\Delta_\alpha$; ψ=0, . . . , Ψ−1 is the index of the individual projections in the parallel-beam system; Ψ is the maximum number of projections; $\Delta_\alpha$ is the angular distance between projections.

In order to convert the real measurement values to the parallel system we interpolate parallel projection values from the immediate neighborhood of the determined pair $(s_l, \alpha_\psi)$, based on a group of four projection values: $\lambda(s^\uparrow, \alpha^\uparrow)$, $\lambda(s^\uparrow, \alpha^\downarrow)$, $\lambda(s^\downarrow, \alpha^\uparrow)$ and $\lambda(s^\downarrow, \alpha^\downarrow)$, where $\alpha^\downarrow$ is the next value below $\alpha_\psi$, $\alpha^\uparrow$ is the next value above $\alpha_\psi$, $s^\downarrow$ is the next value below $s_l$, $s^\uparrow$ is the next value above $s_l$. We can use bilinear interpolation, for instance, to estimate the projection value of the hypothetical ray, according to the following relation:

$$\hat{\lambda}(s_l, \alpha_\psi) \cong \frac{\alpha_\psi - \alpha^\downarrow}{\alpha^\uparrow - \alpha^\downarrow}\left(\frac{s_l - s^\downarrow}{s^\uparrow - s^\downarrow}\lambda(s^\uparrow, \alpha^\uparrow) + \frac{s^\uparrow - s_l}{s^\uparrow - s^\downarrow}\lambda(s^\downarrow, \alpha^\uparrow)\right) + \frac{\alpha^\uparrow - \alpha_\psi}{\alpha^\uparrow - \alpha^\downarrow}\left(\frac{s_l - s^\downarrow}{s^\uparrow - s^\downarrow}\lambda(s^\uparrow, \alpha^\downarrow) + \frac{s^\uparrow - s_l}{s^\uparrow - s^\downarrow}\lambda(s^\downarrow, \alpha^\downarrow)\right), \quad (13)$$

where $\hat{\lambda}(s_l, \alpha_\psi)$ is the interpolated value of the hypothetical parallel system.

The output of this step is a set of the measurements $\hat{\lambda}(s_l, \alpha_\psi)$; l=−L/2, . . . , L/2; ψ=0, . . . , Ψ−1, determined for the hypothetical parallel measurement system.

Step 5

The next part of the reconstruction algorithm of the invention begins by performing the back-projection operation. This operation is described by the following relation:

$$\tilde{f}_{i,j} = \Delta_\alpha \sum_\psi \overline{\lambda}(s_{ij}, \alpha_\psi), \tag{14}$$

where: $\tilde{f}_{i,j}$ is the image of the cross-section obtained after the back-projection operation at position $z_p$, for voxels described by coordinates $(i, j, z_p)$; $i=1, 2, \ldots, I$; $j=1, 2, \ldots, I$; and the measurements $\overline{\lambda}(s_{ij}, \alpha_\psi)$ are interpolated for all pixels (i, j) in the reconstructed image at every angle $\alpha_\psi$ using the following interpolation formula:

$$\overline{\lambda}(s_{ij}, \alpha_\psi) \cong \frac{s_{ij} - s^\downarrow}{\Delta_{xy}} \lambda(s^\uparrow, \alpha_\psi) + \frac{s^\uparrow - s_{ij}}{\Delta_{xy}} \lambda(s^\downarrow, \alpha_\psi), \tag{15}$$

where $s^\downarrow$ is the next value below $s_{ij}$, $s^\uparrow$ is the next value above $s_{ij}$, and $$s_{ij} = \left(i - \frac{I}{2}\right)\Delta_{xy}\cos(\psi\Delta_\psi) + \left(j - \frac{I}{2}\right)\Delta_{xy}\sin(\psi\Delta_\psi). \tag{16}$$

The output of this step is the image $\tilde{f}_{i,j}$; $i=1, 2, \ldots, I$; $j=1, 2, \ldots, I$, i.e. the image obtained after the back-projection operation at position $z_p$.

Figure 6:
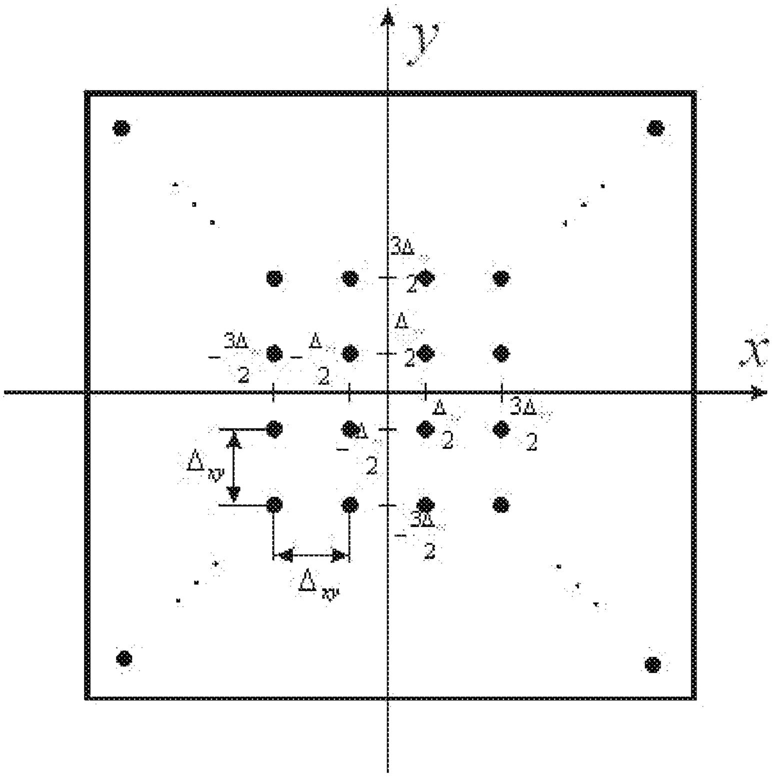
FIG. 6. illustrates schematically the proposed topology of the pixels in the reconstructed image.

The invention presented here relates also to the technical problem of how to avoid the consequences of the central pixel in the reconstructed image being preferred over others during the calculation of coefficients $h_{\Delta i,\Delta j}$ performed in Step 1. Because relation (6) prefers the central point of the (x,y) coordinate system, the pixel lying at this point is also preferred over other pixels. This is because it is only at the point lying at the origin of the coordinate system that the interpolation function gets the same value at every angle $\alpha_\psi$. In this invention, in order to avoid the consequences of this preference for the central pixel in the reconstructed image during the calculation of coefficients $h_{\Delta i,\Delta j}$, the topology of the pixels in the reconstructed image presented in FIG. 6 is proposed. This is to avoid the situation where any pixel is placed at the central point of the reconstructed image. These pixels are placed in this image according to the following description:

$$x = \ldots, -\frac{5\Delta_{xy}}{2}, -\frac{3\Delta_{xy}}{2}, -\frac{\Delta_{xy}}{2}, \frac{\Delta_{xy}}{2}, \frac{3\Delta_{xy}}{2}, \frac{5\Delta_{xy}}{2}, \ldots,$$

for the x direction, and $$y = \ldots, -\frac{5\Delta_{xy}}{2}, -\frac{3\Delta_{xy}}{2}, -\frac{\Delta_{xy}}{2}, \frac{\Delta_{xy}}{2}, \frac{3\Delta_{xy}}{2}, \frac{5\Delta_{xy}}{2}, \ldots$$

for they direction, if the reconstructed image has dimensions I×I (I is chosen to be equal to a positive integer power of 2).

Step 6

In this step, the initial image for the iterative reconstruction procedure is determined. It can be any image $$f_{i,j}^0$$

but in order to accelerate the reconstruction process it is determined using a standard reconstruction method based on the measurements $\lambda(s, \alpha)$, for instance the well-known FBP method.

The output of this step is the initial reconstructed image $$f_{i,j}^0;\ i = 1, 2, \ldots, I;\ j = 1, 2, \ldots, I.$$

Step 7

The reconstructed image $$f_{i,j}^t$$

can be processed by the iterative reconstruction process as a sub-procedure of the reconstruction algorithm using the matrix $H_{ij}$. The image obtained in Step 6 is used as the initial image $$f_{i,j}^0$$

for this sub-procedure.

The output of this step is the reconstructed image $$f_{i,j}^{t\_stop};\ i = 1, 2, \ldots, I;\ j = 1, 2, \ldots, I.$$

The image obtained in this way is destined to be presented on a screen for diagnostic interpretation using a different method of presentation developed for PET imaging techniques.

Figure 7:
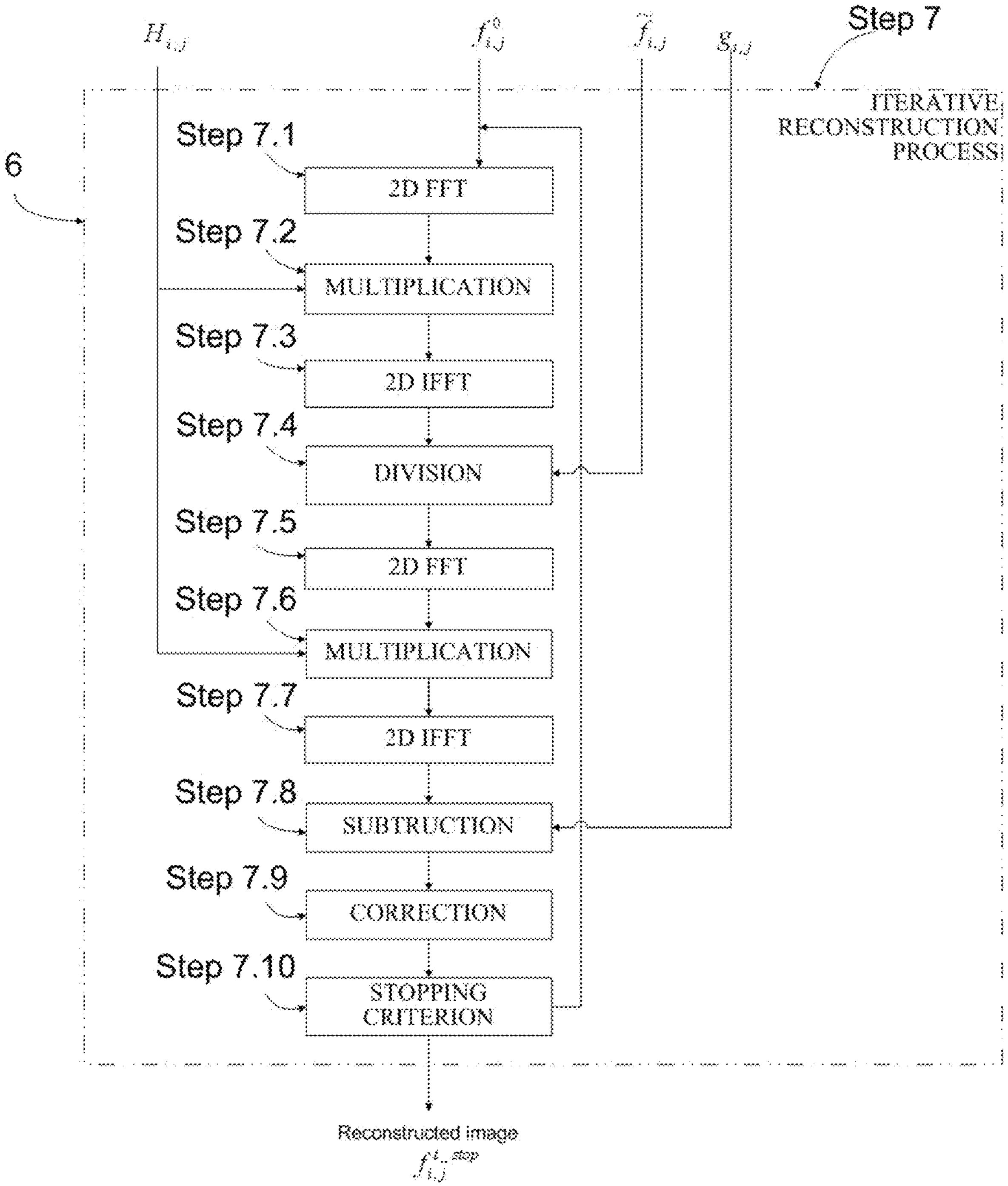
FIG. 7. depicts the block schematic diagram of an iterative reconstruction process.

The iterative reconstruction procedure performed in Step 7 consists of several sub-operations as presented in FIG. 7, as follows.

Step 7.1

At the beginning of every iteration of this sub-procedure, the 2D FFT of the reconstructed image $$f_{i,j}^t$$

is performed. Of course, at the first iteration, the image $$f_{i,j}^0$$

is transformed.

If the reconstructed image has dimensions I×I then the frequency representation of this image $$F_{k,l}^t$$

has dimensions 2I×2I.

Step 7.2

In this step, every element of the matrix $$F^t_{k,l}$$

is multiplied by the corresponding element of the matrix $H_{k,l}$ (obtained in Step 3). This operation represents a convolution operation transformed to the frequency domain. This drastically reduces the number of calculations necessary.

In this way, $4I^2$ multiplications produce the matrix $$B^t_{k,l}$$

with dimensions 2I×2I.

Step 7.3

In this step, the inverse 2D FFT of the matrix $$B^t_{k,l}$$

is performed.

If the matrix $$B^t_{k,l}$$

has dimensions 2I×2I then the spatial representation of this matrix $$b^t_{i,j}$$

has dimensions I×I.

Step 7.4

In this step, all values of the matrix $\tilde{f}_{i,j}$, obtained in Step 5, are divided by the corresponding elements of the matrix $$b^t_{i,j},$$

in the following way:

$$c^t_{i,j} = \frac{\tilde{f}_{i,j}}{b^t_{i,j}}, \tag{17}$$

The result of this operation is the matrix $$c^t_{i,j}$$

with dimensions I×I.

Step 7.5

The 2D FFT of the matrix $$c^t_{i,j}$$

is performed

If the reconstructed image has dimensions I×I then the frequency representation of this matrix $$C^t_{k,l}$$

has dimensions 2I×2I.

Step 7.6

In this step, every element of the matrix $$C^t_{k,l}$$

is multiplied by the corresponding element of the matrix $H_{kl}$ (obtained in Step 3). This operation represents a convolution operation transformed to the frequency domain. This drastically reduces the number of calculations necessary.

In this way, $4I^2$ multiplications produce the matrix $$D^t_{k,l}$$

with dimensions 2I×2I.

Step 7.7

In this step, the inverse 2D FFT of the matrix $$D^t_{k,l}$$

is performed and the matrix $$d^t_{i,j}$$

in the spatial domain is obtained.

If the matrix $$D^t_{kl}$$

has dimensions 2I×2I then the spatial representation of this matrix $$d^t_{i,j}$$

has dimensions I×I.

Step 7.8

In this step, from every element of the matrix $$d_{i,j}^{t}$$

the corresponding element of the matrix $g_{i,j}$ (obtained in Step 2) is subtracted.

The result of this operation is the matrix $$e_{i,j}^{t}$$

with dimensions I×I.

Step 7.9

A correction operation is performed in this step, according to the following relation $$f_{i,j}^{t+1} = f_{i,j}^{t} - \rho \cdot e_{i,j}^{t}, \tag{18}$$

where ρ is a constant coefficient.

The output for this step is the next estimation of the reconstructed image $$f_{i,j}^{t+1};\ i = 1, 2, \ldots, I;\ j = 1, 2, \ldots, I.$$

Step 7.10

In this step, a decision is made as to whether the iterative process is to continue or not. This decision can be made based on a subjective evaluation of the reconstructed image quality at this stage of the reconstruction process (whether the quality of reconstructed image is satisfactory). Alternatively, the reconstruction process can be stopped after a number of iterations established in advance.

If the reconstruction process is continued, then image $$f_{i,j}^{t+1}$$

is the input matrix (representing the reconstructed image) for the next iteration of the iterative reconstruction process 8, i.e.

$$f_{i,j}^{t} = f_{i,j}^{t+1},$$

or if it is not continued, then image $$f_{i,j}^{t+1}$$

is considered to be the final reconstructed image, i.e.

$$f_{i,j}^{t\_stop} = f_{i,j}^{t+1}.$$

Figure 8:
FIG. 8 is a prior art reconstructed image of a mathematical phantom using a FBP-type reconstruction algorithm.
Figure 9:
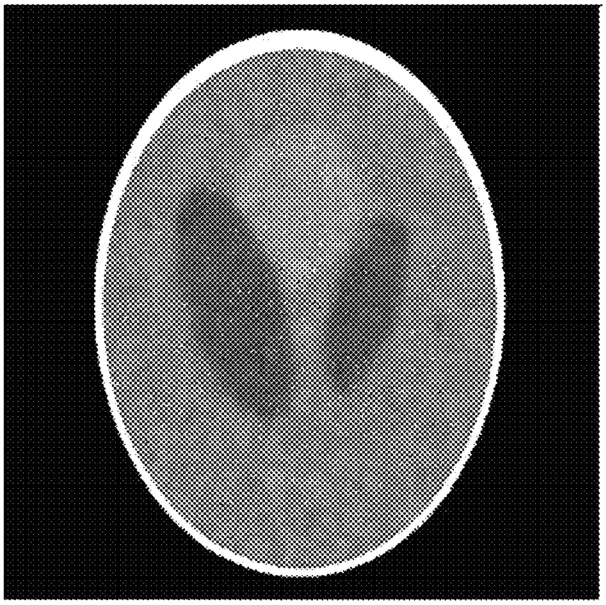
FIG. 9 is a reconstructed image of a mathematical phantom using the reconstruction method which embodies the presented invention.

Using this image reconstruction method and apparatus to practice the invention presented here, image artifacts and distortion are significantly reduced, as shown by the contrast between FIG. 8 and FIG. 9. In consequence, this improves the resolution of the reconstructed images and/or decreases the tracer dosage absorbed by a patient during the examination, while maintaining the quality of the PET images obtained. This is because the dosage is strongly related to the resolution of the images obtained. Furthermore, in contrast to the traditional algebraic approach, where the computational complexity of every iteration of the reconstruction procedure is approximately proportional to $I^4$×number of measurements made for each iteration, our method is very attractive (it is feasible and gives high quality images) and only has a computational complexity of approximately $8I^2 \log_2 I$ for each iteration of the iterative reconstruction process. This computational reduction is achieved thanks to the use of the FFT and IFFT algorithms during each iteration of our iterative reconstruction procedure.

REFERENCES CITED

U.S PATENT DOCUMENTS

| | | | |
|---|---|---|---|
| 9,508,164 | B2 | November 2016 | Cierniak |
| 10,573,029 | B2 | February 2020 | Cierniak |
| 7,769,217 | B2 | August 2010 | Hamill et al. |

OTHER PUBLICATIONS

[1] K. Sauer, C. Bouman, A *local update strategy for iterative reconstruction from projections*, IEEE Transactions on Signal Processing, vol. 41, No. 3, pp. 534-548, 1993.

[2] J. A. Fessler, Penalized weighted least-squares image reconstruction for positron emission tomography, IEEE Transactions on Medical Imaging, vol. 13, No. 2, pp. 290-300, 1994.

[3] L. A. Shepp, Y. Vardi, Maximum likelihood reconstruction for emission tomography, IEEE Transactions on Medical Imaging, vol. MI-1, No. 2, pp. 113-122, 1982.

[4]P. J. Green, Bayesian reconstructions from emission tomography data using a modified EM algorithm, IEEE Transactions on Medical Imaging, vol. 9, No. 1, pp. 84-93, 1990.

[5] R. Cierniak, *New neural network algorithm for image reconstruction from fan-beam projections*, Neurocomputing, vol. 72, pp. 3238-3244, 2009.

[6] R. Cierniak, *A new approach to tomographic image reconstruction using a Hopfield-type neural network*, International Journal Artificial Intelligence in Medicine, vol. 43, No. 2, pp. 113-125, 2008.

[7] R. Cierniak, *A three-dimensional neural network based approach to the image reconstruction from projections problem*, Lecture Notes in Artificial Intelligence 6113, s. 505-514, Springer Verlag, 2010.

[8] Dobosz P., Cierniak R., *Using of EM algorithm to image reconstruction problem with tomography noises*, $5^{th}$ International Conference on Image Processing & Communications, Bydgoszcz, 11-13.IX.2013, In: Image Processing and Communications Challenges 5. Ed. Ryszard S. Choras, pp. 37-43, Advances in Soft Computing Series, vol. 233, Springer, Cham, 2013.

[9] Zeng L., Extension of emission EM look-alike algorithms to Bayesian Algorithms, 17th International Meeting on Fully Three-Dimensional Image Reconstruction in Radiology and Nuclear Medicine, Proc. SPIE vol. 11072, 2019.

The invention claimed is:

1. A method for performing an iterative reconstruction process, forming part of a method for reconstructing an image of an examined object using a positron emission tomography scanner, is carried out by a procedure comprising of:

performing a 2-dimensional (2D) FFT of a reconstructed image represented by a matrix $$f_{i,j}^{t};$$

a resulting matrix $$F_{k,l}^{t}$$

is a frequency representation or the matrix $$f_{i,j}^{t};$$

multiplying elements of the resulting matrix $$F_{k,l}^{t}$$

which are obtained in the previous step of the iterative reconstruction process by corresponding elements of a matrix $H_{k,l}$ which is obtained using a 2D FFT of a matrix $h_{\Delta i,\Delta j}$ whose elements are determined, before the iterative reconstruction process is started; a matrix $$B_{k,l}^{t}$$

is a frequency representation of a referential matrix $$b_{i,j}^{t}$$

for an image obtained after a back-projection operation, represented by a matrix $\tilde{f}_{i,j}$;

performing a 2D IFFT of the matrix $$B_{k,l}^{t}$$

obtained in the previous step of the iterative reconstruction process; a resulting matrix represents the referential matrix $$b_{i,j}^{t}$$

for the image obtained after the back-projection operation, represented by the matrix $\tilde{f}_{i,j}$;

dividing all the values of the matrix $\tilde{f}_{i,j}$, obtained after the back-projection operation, by the corresponding elements of the matrix $$b_{i,j}^{t},$$

obtained as a result of the previous step of the iterative reconstruction process; the resulting matrix is a matrix $$c_{i,j}^{t};$$

performing a 2D FFT of the matrix $$c_{i,j}^{t}$$

obtained in the previous step of the iterative reconstruction process; a matrix $$C_{k,l}^{t}$$

is a frequency representation of the matrix $$c_{i,j}^{t};$$

multiplying the elements of the matrix $$C_{k,l}^{t},$$

obtained in the previous step of the iterative reconstruction process, by the corresponding elements of the matrix $H_{k,l}$ which is obtained using a 2D FFT of the matrix $h_{\Delta i,\Delta j}$ whose elements are determined, before the iterative reconstruction process is started; a matrix $$D_{k,l}^{t}$$

is a frequency representation of a biased correction matrix for the reconstructed image represented by the matrix $$f_{i,j}^{t};$$

performing a 2D IFFT of the matrix $$D^t_{k,l}$$

obtained in the previous step or the iterative reconstruction process; a resulting matrix $$d^t_{i,j}$$

represents the biased correction matrix for the reconstructed image represented by the matrix $$f^t_{i,j};$$

subtracting from all the values of the matrix $$d^t_{i,j},$$

obtained as a result of the previous step of the iterative reconstruction process, the corresponding elements of a matrix $g_{i,j}$ whose elements are determined, before the iterative reconstruction process is started; is a matrix the resulting matrix $$e^t_{i,j};$$

performing a correction of the reconstructed image represented by the matrix $$f^t_{i,j}$$

using corresponding elements of the matrix $$e^t_{i,j},$$

obtained as a result of the previous step of the iterative reconstruction process;

using a criterion for stopping the iterative process.

2. A method of performing an iterative reconstruction process, which forms part of a method of tomographic imaging, is carried out by steps which comprise:

performing a 2-dimensional (2D) FFT of a reconstructed image represented by a matrix $$f^t_{i,j};$$

a resulting matrix $$F^t_{k,l}$$

is a frequency representation or the matrix $$f^t_{i,j};$$

multiplying elements of the resulting matrix $$F^t_{k,l}$$

which are obtained in the previous step of the iterative reconstruction process by corresponding elements of a matrix $H_{k,l}$ which is obtained using a 2D FFT of a matrix $h_{\Delta i,\Delta j}$ whose elements are determined, before the iterative reconstruction process is started; a matrix $$B^t_{k,l}$$

is a frequency representation of a referential matrix $$b^t_{i,j}$$

for an image obtained atter a back-projection operation, represented by a matrix $\tilde{f}_{i,j}$;

performing a 2D IFFT of the matrix $$B^t_{k,l}$$

obtained in the previous step of the iterative reconstruction process; a resulting matrix represents the referential matrix $$b^t_{i,j}$$

for the image obtained from the back-projection operation, represented by the matrix $\tilde{f}_{i,j}$;

dividing all the values of the matrix $\tilde{f}_{i,j}$, obtained after the back-projection operation, by the corresponding elements of the matrix $$b^t_{i,j},$$

obtained as a result of the previous step of the iterative reconstruction process; the resulting matrix is a matrix $$c^t_{i,j};$$

performing a 2D FFT of the matrix $$c^t_{i,j}$$

obtained in the previous step of the iterative reconstruction process; a resulting matrix $$C_{k,l}^{t}$$

is a frequency representation or the matrix $$c_{i,j}^{t};$$

multiplying the elements of the matrix $$C_{k,l}^{t},$$

obtained in the previous step of the iterative reconstruction process, by the corresponding elements of the matrix $H_{k,l}$ which is obtained using a 2D FFT of the matrix $h_{\Delta i,\Delta j}$ whose elements are determined, before the iterative reconstruction process is started; a matrix $$D_{k,l}^{t}$$

is a frequency representation of a biased correction matrix for the reconstructed image represented by the matrix $$f_{i,j}^{t};$$

performing a 2D IFFT of the matrix $$D_{k,l}^{t}$$

obtained in the previous step or the iterative reconstruction process; a resulting matrix $$d_{i,j}^{t}$$

represents the biased correction matrix for the reconstructed image represented by the matrix $$f_{i,j}^{t};$$

subtracting from all the values of the matrix $$d_{i,j}^{t},$$

obtained as a result of the previous step of the iterative reconstruction process, the corresponding elements of a matrix $g_{i,j}$ whose elements are determined, before the iterative reconstruction process is started; is a matrix the resulting matrix $$e_{i,j}^{t};$$

performing a correction of the reconstructed image represented by the matrix $$f_{i,j}^{t}$$

using corresponding elements of the matrix $$e_{i,j}^{t},$$

obtained as a result of the previous step of the iterative reconstruction process;

using a criterion for stopping the iterative process.

* * * * *